United States Patent
Hasem et al.

(10) Patent No.: US 6,941,804 B2
(45) Date of Patent: Sep. 13, 2005

(54) DETERMINING THE PVT PROPERTIES OF A HYDROCARBON RESERVOIR FLUID

(75) Inventors: Mohamed Naguib Hasem, Mandeville, LA (US); Gustavo Antonio Ugueto, Mandeville, LA (US)

(73) Assignee: Shell Oil Company, Houston, TX (US)

( * ) Notice: Subject to any disclaimer, the term of this patent is extended or adjusted under 35 U.S.C. 154(b) by 49 days.

(21) Appl. No.: 10/363,952

(22) PCT Filed: Jan. 17, 2002

(86) PCT No.: PCT/EP02/00517

§ 371 (c)(1),
(2), (4) Date: Mar. 6, 2003

(87) PCT Pub. No.: WO02/057596

PCT Pub. Date: Jul. 25, 2002

(65) Prior Publication Data

US 2004/0029739 A1 Feb. 12, 2004

Related U.S. Application Data

(60) Provisional application No. 60/302,982, filed on Jul. 3, 2001.

(30) Foreign Application Priority Data

Jan. 18, 2001 (EP) .............................. 01200180

(51) Int. Cl.[7] .............................. G01N 1/10; G01N 7/00; G06F 17/17

(52) U.S. Cl. ................. 73/152.24; 73/152.23; 73/152.27; 73/152.28; 73/152.51; 73/152.52; 73/152.53; 73/152.54; 175/48; 175/50; 175/58; 175/59; 175/60

(58) Field of Search .......... 73/152.01, 152.23, 73/152.24, 152.26, 152.27, 152.28, 152.51, 152.53, 152.54, 152.55, 152.57; 175/48, 50, 58, 59, 60

(56) References Cited

U.S. PATENT DOCUMENTS

| | | | | |
|---|---|---|---|---|
| 3,079,085 A | * | 2/1963 | Clark et al. | 703/10 |
| 4,267,726 A | * | 5/1981 | Noik | 73/152.31 |
| 4,413,512 A | * | 11/1983 | Zemanek, Jr. | 73/152.08 |
| 4,831,530 A | * | 5/1989 | Rai | 702/12 |

(Continued)

OTHER PUBLICATIONS

"Resevoir Characterization Instrument", Baker Hughes, 2000, pp. 1–16.*
Hurst et al., "Using the Cased–hole Formation Tester Tool for Pressure Transient Analysis", SPE, Inc., 2000, pp. 449–463.*

(Continued)

*Primary Examiner*—Hezron Williams
*Assistant Examiner*—David A. Rogers

(57) ABSTRACT

A method of determining an in situ PVT property of a hydrocarbon reservoir fluid that is present in a hydrocarbon-bearing formation layer traversed by a borehole, which method involves the steps of:

a) calculating along the hydrocarbon-bearing formation layer the pressure gradient; and b) determining the in situ PVT property from the pressure gradient using an empirical relation that had been obtained by fitting a curve (11) through previously obtained data points (12, 13, 14) having the measured PVT property as a function of the pressure gradient.

5 Claims, 6 Drawing Sheets

U.S. PATENT DOCUMENTS

| | | | | |
|---|---|---|---|---|
| 4,903,207 | A | * | 2/1990 | Alger et al. ............... 702/13 |
| 5,337,821 | A | * | 8/1994 | Peterson ............... 166/250.07 |
| 5,353,875 | A | * | 10/1994 | Schultz et al. ............... 166/297 |
| 5,778,154 | A | | 7/1998 | Bone et al. |
| 5,828,981 | A | * | 10/1998 | Callender et al. ............... 702/6 |
| 6,070,662 | A | * | 6/2000 | Ciglenec et al. ......... 166/254.1 |
| 6,101,447 | A | * | 8/2000 | Poe, Jr. ............... 702/13 |
| 6,393,906 | B1 | * | 5/2002 | Vityk et al. ............... 73/152.51 |
| 6,755,246 | B2 | * | 6/2004 | Chen et al. ............... 166/250.01 |
| 2003/0182061 | A1 | * | 9/2003 | Ferworn et al. ............... 702/12 |

OTHER PUBLICATIONS

El–Banbi et al., "Sampling Oil Wells", SPE, Inc., 2001, pp. 1–6.*

Diatschenko, Victor, "PVT–Comparison of Estimated to Measured Fluid Properties", Southwestern Petroleum Short Course, 1999, pp. 307–320.*

Ghorbani et al., "Fluid Characterization of an Iranian Carbonate Oil Resevoir Using Different PVT Packages", SPE, Inc., 2001, pp. 1–7.*

Gozalpour, et al., "Predicting Resevoir Fluid Phase and Volumetric Behaviour from Samples Contaminated with Oil–Based Mud", SPE, Inc., 1999, pp. 357–365.*

Mahmood et al., "Evaluation of Empirically Derived PVT Properties for Pakistani Crude Oils", Journal of Petroleum Science and Engineering, 1996, pp. 275–290.*

Dorshow, Richard B., "The Simultaneous Measurement of Interfacial Tension and Oil Viscosity at Reservoir Conditions . . . ", 1995, SPE Advanced Technologies, vol. 3, No. 1, pp. 120–128.*

Crombie et al., "Innovations in Wireline Fluid Sampling", 1998, Oilfield Review, pp. 26–41.*

Hashem, Mohamed, "Determination of Producible Hydrocarbon Type and Oil Quantity in Wells Drilled with Synthetic Oil–Based Muds", 1997, SPE Annual Technical Conference, pp. 353–366.*

Van Dusen, Alexandra, "Determination of Hydrocarbon Properties by Optical Analysis During Wireline Fluid Sampling", 2000, SPE Annual Technical Conference, pp. 773–785.*

Ridha B.C., Gharbi, et al: "Neural Network Model for Estimating the PVT Properties of Middle East Crude Oils", SPE Reservoir Eval. & Eng.#56850, vol. 2, No. 3, Jun. 1999 pp. 255–265.

N. Varotsis: "A Novel Non–Iterative Method for the Prediction of the PVT Behavior of Reservoir Fluids", SPE #56745, Oct. 3, 199, pp. 1–9.

* cited by examiner

DETERMINING THE PVT PROPERTIES OF A HYDROCARBON RESERVOIR FLUID

The present application claims priority on European Patent Application 01200180.6, filed on 18 Jan. 2001.

FIELD OF INVENTION

The present invention relates to determining the PVT properties of a hydrocarbon reservoir fluid, where PVT is an acronym used to refer to pressure, volume and temperature. PVT properties are gas-oil ratio, API gravity, viscosity, saturation pressure, formation volume factor, molecular weight, density and oil compressibility.

BACKGROUND OF INVENTION

In order to measure the PVT properties of a hydrocarbon reservoir fluid, a sample of the reservoir fluid is taken and analysed under reservoir pressure and temperature. A brief description of the way in which a PVT analysis is carried out is given in section 3 of the book Contributions in Petroleum Geology and Engineering, Volume 5, Properties of Oils and Natural Gases, K. S. Pederson et al, 1989. Such an analysis can be very accurate, however it takes a long time to be completed.

It is of great importance to know the PVT properties of the reservoir fluid as soon as possible, preferably directly after a well has been drilled. Knowing such information allows for the adjustment of the design of the production and surface equipment to take into account the actual PVT properties.

SUMMARY OF THE INVENTION

Applicant has found that there are empirical relations between the PVT properties and the pressure gradient (dp/dz) in the reservoir, wherein p is the fluid pressure in the reservoir and z the true vertical depth. Because the pressure gradient can be determined directly after completing drilling, the PVT properties can be obtained as early as possible.

Thereto the method of determining at least one of the in situ PVT properties of a hydrocarbon reservoir fluid that is present in a hydrocarbon-bearing formation layer traversed by a borehole according to the present invention comprises the steps of:

a) calculating along the hydrocarbon-bearing formation layer the pressure gradient; and
b) determining the in situ PVT property from the pressure gradient using an empirical relation that had been obtained by fitting a curve through previously obtained data points comprising the measured PVT property as a function of the pressure gradient.

BRIEF DESCRIPTION OF DRAWINGS

The method will now be described by way of example with reference to the accompanying drawings in which the examples should not be construed to limit the scope of the invention.

DETAILED DESCRIPTION OF THE PREFERRED EMBODIMENTS

With reference to the Figures, we will now discuss the method of determining at least one of the in situ PVT properties according to the present invention in reverse order, wherein we start with discussing how the empirical relation is obtained.

Figure 1:
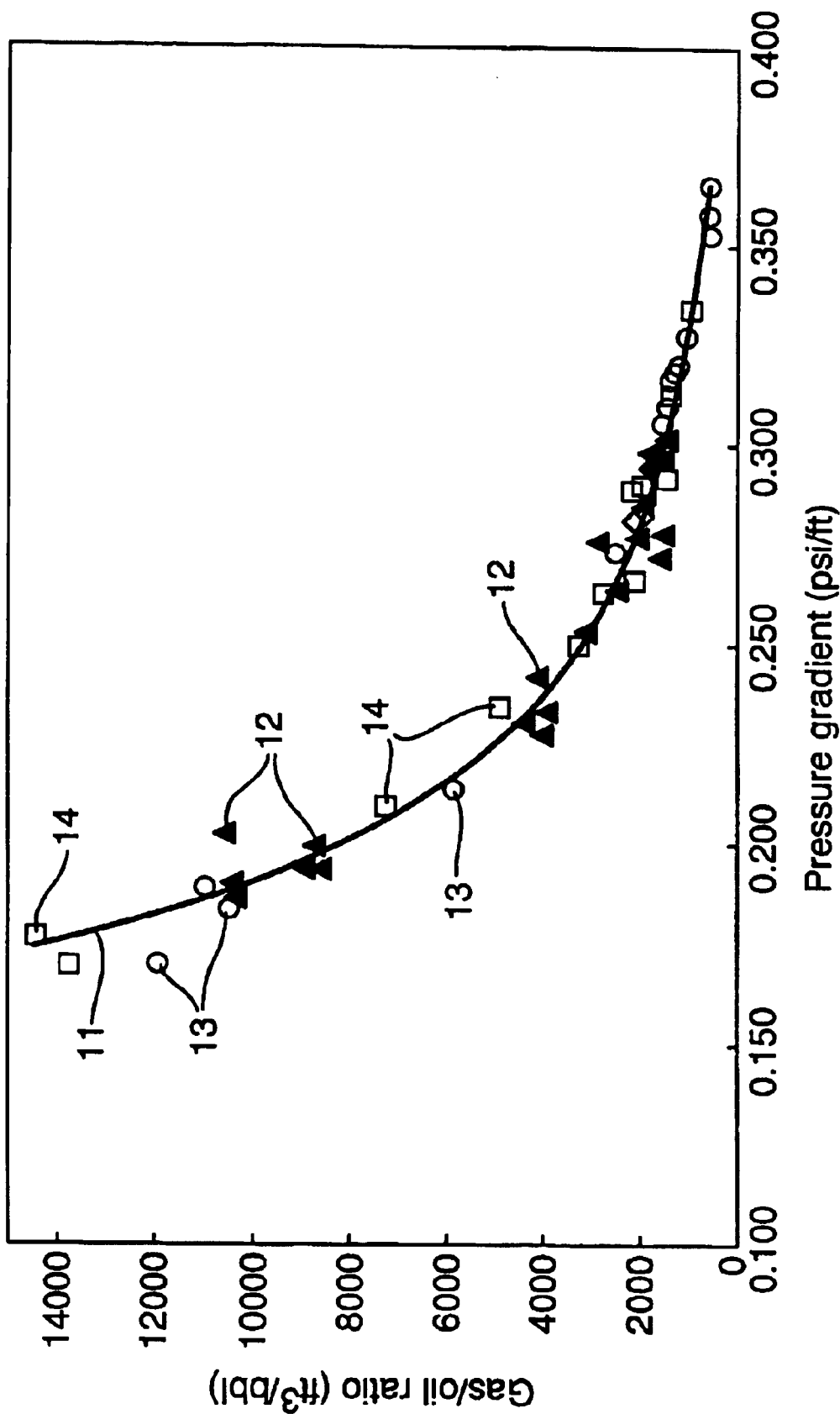
FIG. 1 shows the gas-oil ratio in standard cubic feet per standard barrel on the y-axis as a function of the pressure gradient in psi per foot (at in situ pressure and temperature) on the x-axis.
Figure 2:
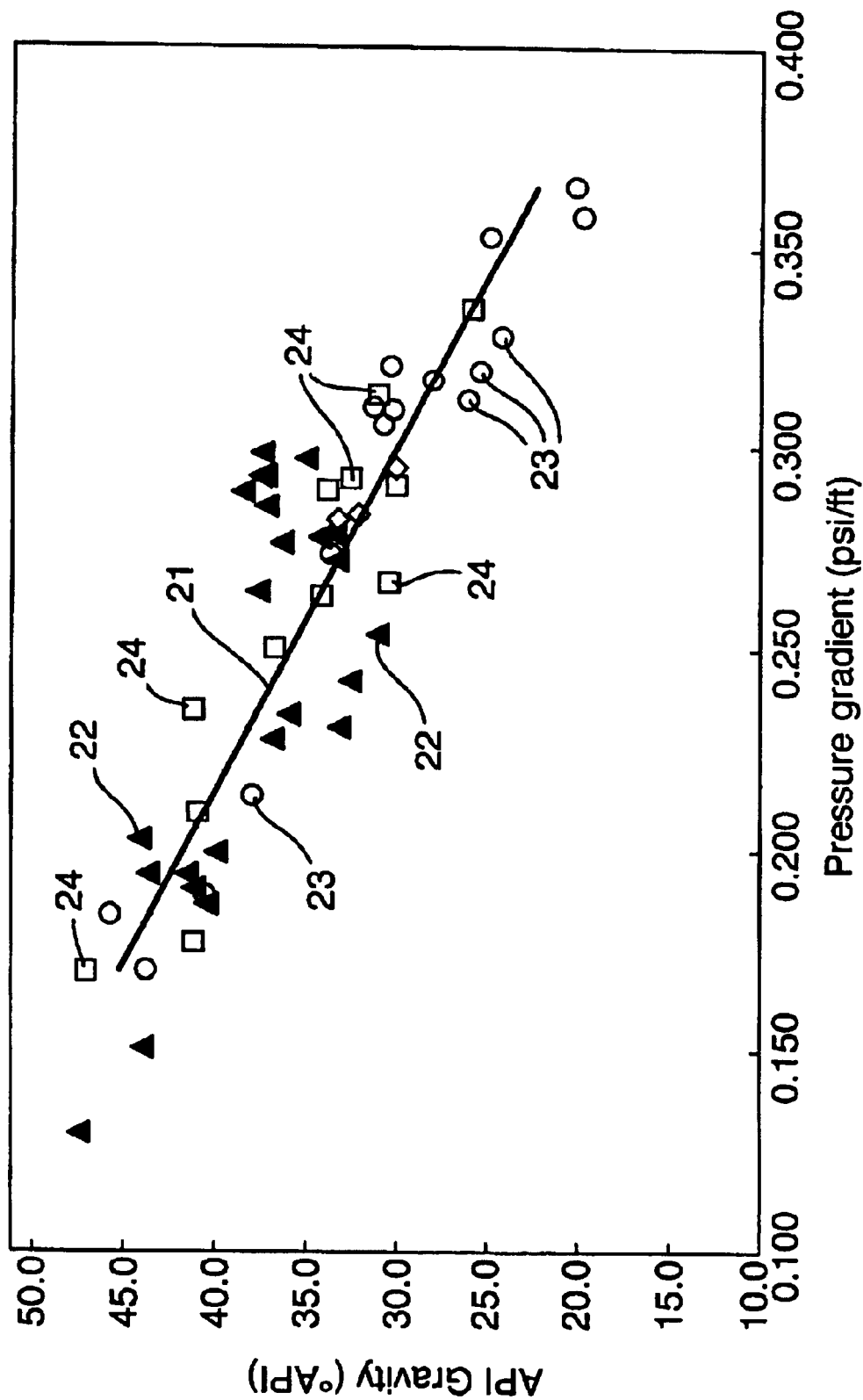
FIG. 2 shows the API gravity in °API on the y-axis as a function of the pressure gradient in psi per foot (at in situ pressure and temperature) on the x-axis.
Figure 3:
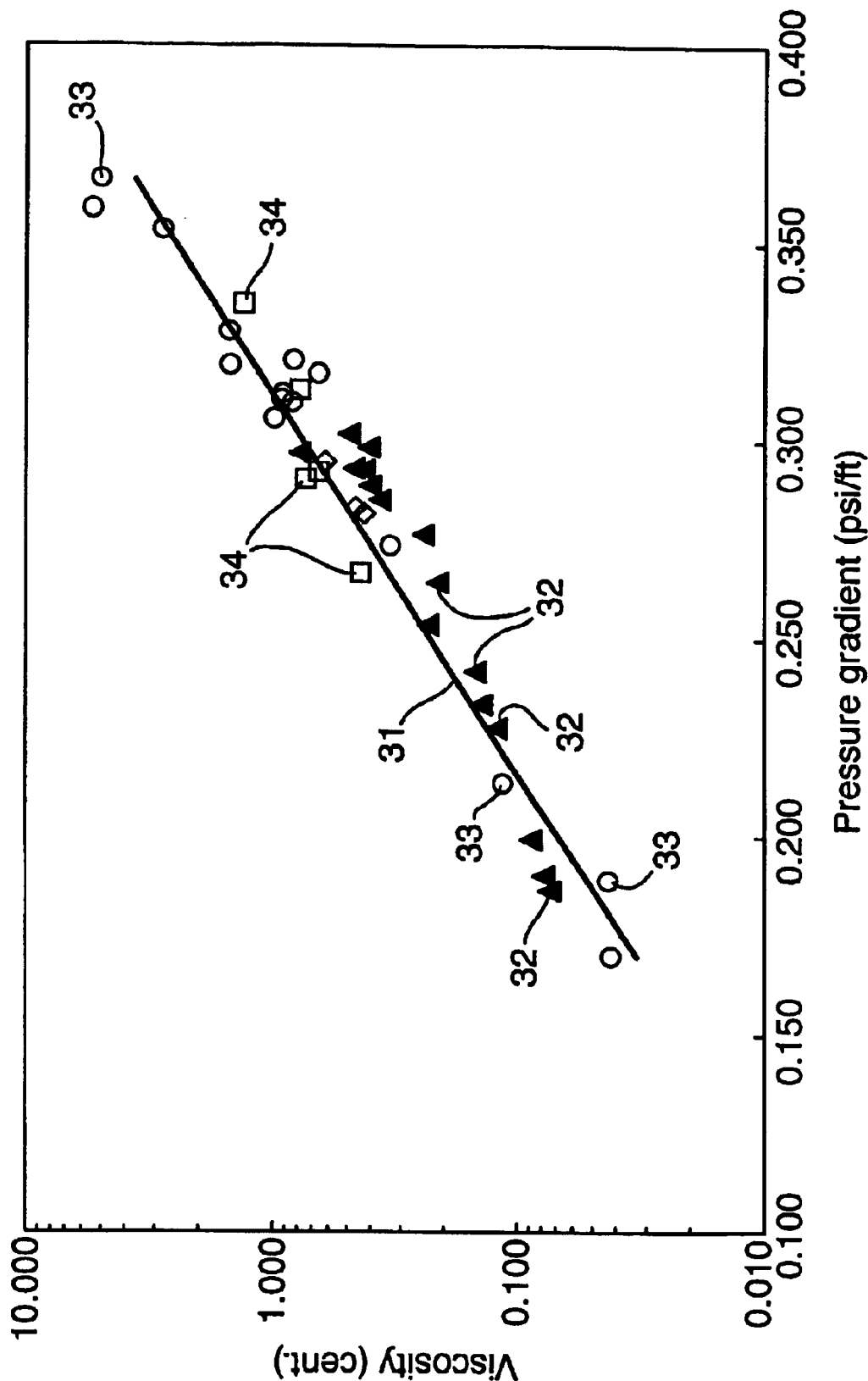
FIG. 3 shows the viscosity in centipoise (at in situ pressure and temperature) on the y-axis as a function of the pressure gradient in psi per foot (at in situ pressure and temperature) on the x-axis.
Figure 4:
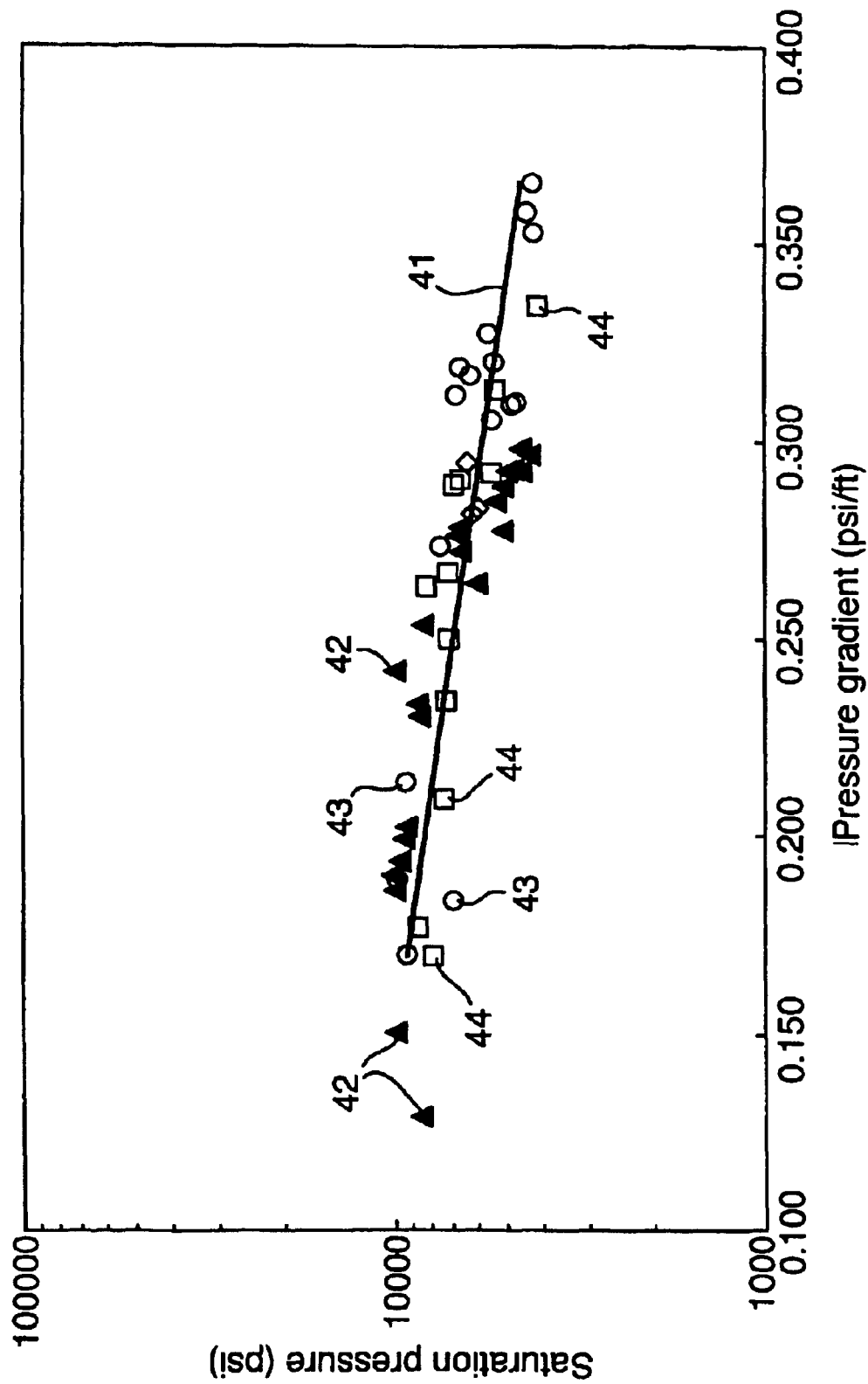
FIG. 4 shows the saturation pressure in psi absolute on the y-axis as a function of the pressure gradient psi per foot (at in situ pressure and temperature) on the x-axis.
Figure 5:
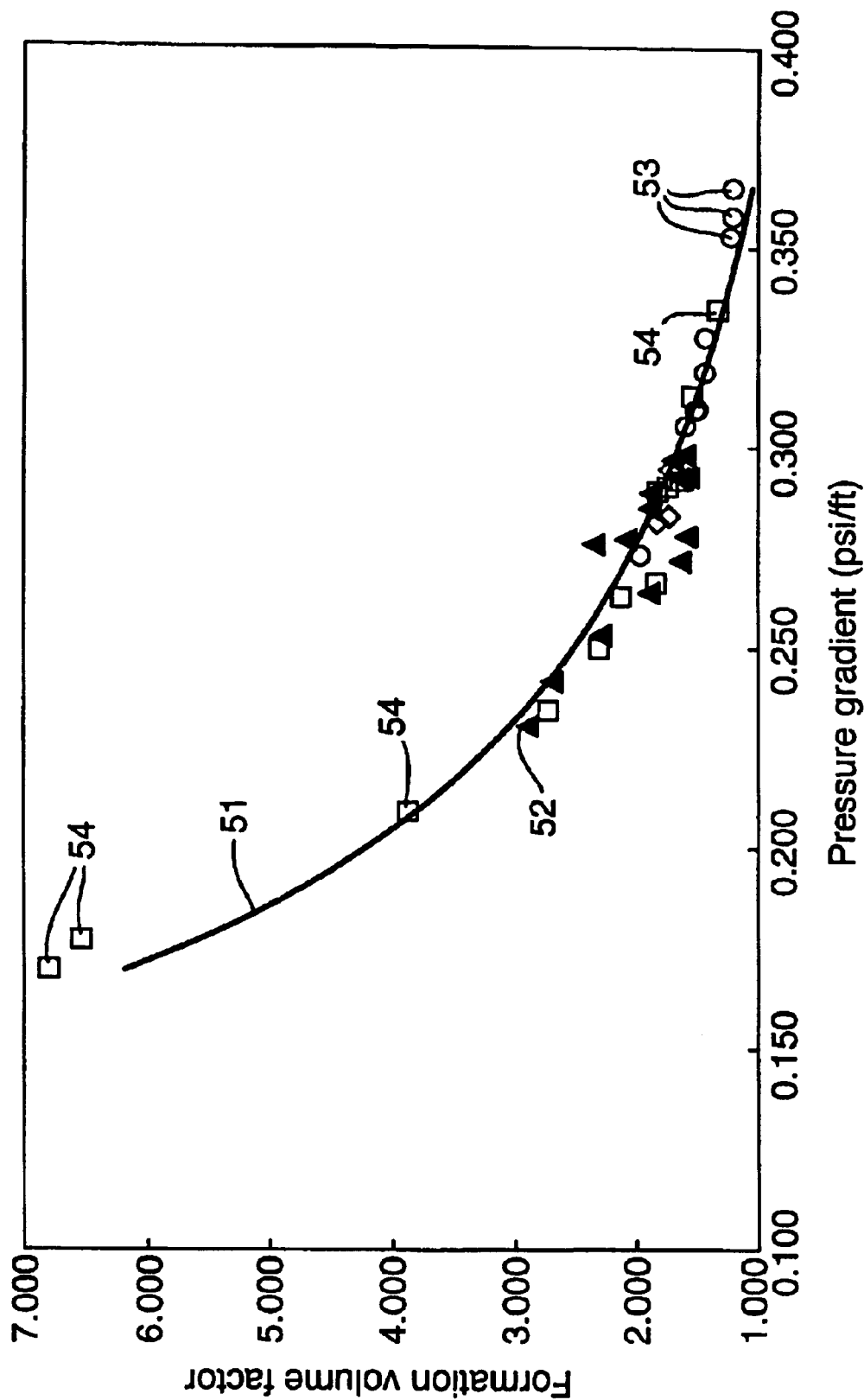
FIG. 5 shows the formation volume factor, oil on the y-axis as a function of the pressure gradient in psi per foot (at in situ pressure and temperature) on the x-axis.
Figure 6:
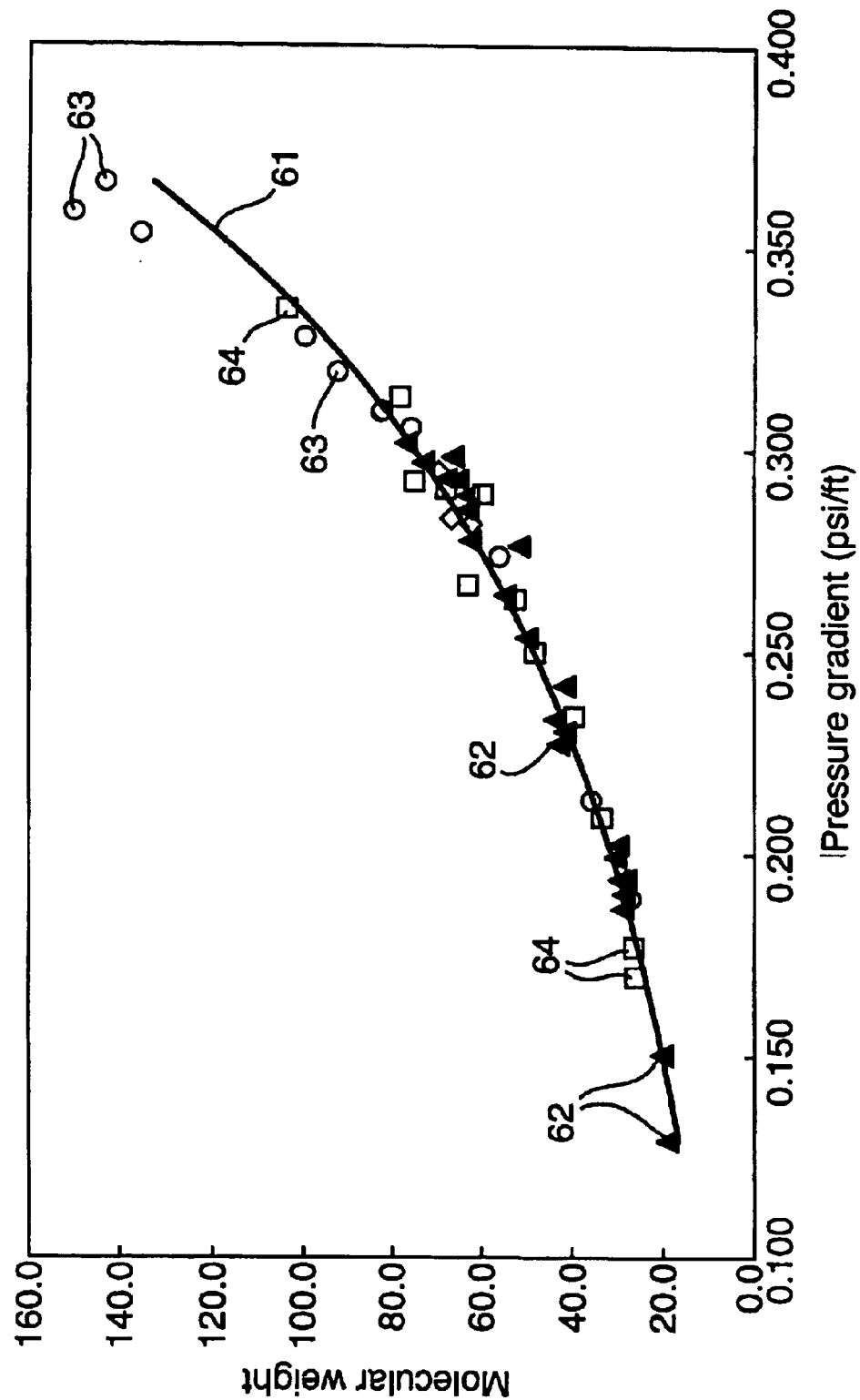
FIG. 6 shows the molecular weight on the y-axis as a function of the pressure gradient psi per foot (at in situ pressure and temperature) on the x-axis.

The curves shown in FIGS. 1-6 show the empirical relation, line i1, that fits the data points i2, i3 and i4, where i is the number of the Figure (i=1–6) obtained from samples taken from reservoirs in the same geological area. For the sake of clarity not all data points have been referred to by a reference numeral.

A data point was obtained as follows. At first a well was drilled to the formation layer containing a hydrocarbon reservoir fluid. Then a tool was lowered to the first of a set of locations in that formation layer by means of for example a wireline. The tool comprises a central conduit having an inlet and being provided with a pressure sensor, and a fluid receptacle having an inlet opening into the central conduit. At the first location an exclusive fluid communication was made between the formation and the inlet of the central conduit by extending into the formation a probe having an outlet that is in direct fluid communication with the inlet of the central conduit. Then formation fluid was allowed to enter into the fluid receptacle and the pressure build-up was measured. The required fluid pressure is the pressure at the end of the pressure build-up for that location.

Then the tool was moved to the next location where the pressure-build up was again measured to obtain the fluid pressure for that location, and so on until all the fluid pressures at all locations had been determined. With this the pressure gradient was determined.

Further, at each location a pressure-build no test was conducted, a sample of the hydrocarbon reservoir fluid was taken, and the PVT properties of the sample were measured in a laboratory under reservoir conditions. Each measurement resulted in a data point that was plotted in FIGS. 1–6.

To get all data points these data were collected and analysed for more wells in the same geological area.

Then for each PVT property a curve was fitted through the data, and surprisingly, the data could be fitted with a considerable accuracy, with a goodness of fit $R^2$ of greater than 0.9, wherein $$R^2 = \frac{\left(\sum_{i=1}^{n}(x_i-x)(y_i-y)\right)^2}{\sum_{i=1}^{n}(x_i-x)^2 \sum_{i=1}^{n}(y_i-y)^2},$$

wherein n is the number of data points, $(x_1, \ldots, x_n)$ is the set of pressure gradients, x is the mean pressure gradient, $(y_1, \ldots, y_n)$ is the set of measurements of the PVT property and y is the mean PVT property. $R^2$ is the squared value of the correlation coefficient.

The below Table gives the results of the curve fitting.

| PVT property | Curve | $R^2$ |
|---|---|---|
| Gas oil ratio | $(8.6)(dp/dz)^{-.42}$ | 0.98 |
| API gravity | $65 - (117)(dp/dz)$ | 0.91 |
| Viscosity | $(0.0005)\exp(24\,dp/dz)$ | 0.96 |
| Saturation pressure | $(16980)\exp(-3.6\,dp/dz)$ | 0.72 |
| Formation volume factor | $(0.10)(dp/dz)^{-.23}$ | 0.97 |
| Molecular weight | $(5.2)\exp(8.9\,dp/dz)$ | 0.98 |

The correlation can as well be obtained for other PVT properties, such as density and oil compressibility.

We now discuss how a PVT property of an unknown hydrocarbon reservoir fluid that is present in a hydrocarbon-bearing formation layer traversed by a borehole is determined in situ. Suitably, the hydrocarbon-bearing formation layer is in the same geological area.

At first a tool is lowered to the first of a set of locations in that formation layer. The tool comprises a central conduit having an inlet and being provided with a pressure sensor, and a fluid receptacle having an inlet opening into the central conduit. At the first location an exclusive fluid communication is made between the formation and the inlet of the central conduit by extending into the formation a probe having an outlet that is in direct fluid communication with the inlet of the central conduit. Then formation fluid is allowed to enter into the fluid receptacle and the pressure build-up was measured. The required fluid pressure is the pressure at the end of the pressure build-up for that location.

Then the tool is moved to the next location where the pressure-build up is again measured to obtain the fluid pressure for that location, and so on until all the fluid pressures at all locations have been determined. With this the pressure gradient is calculated.

Then the pressure gradient is used with the empirical relation to get the PVT property that is required.

This shows that with the method according to the present invention a good accuracy can be achieved.

In case the hydrocarbon reservoir fluid is a so-called heavy oil that is relatively viscous, it will be difficult to acquire a representative sample of the reservoir fluid. In order to obtain a representative sample, the step of making an exclusive fluid communication further includes activating a heating device arranged near the probe to heat the formation fluid.

Suitably, the probe is associated with a packer pad in an assembly, and the heating device is placed in the packer pad. Alternatively the heating device is arranged on the tool. The heating device may be a device generating microwaves, light waves or infrared waves. The heating device may also be an electrical heater, a chemical heater or a nuclear heater.

So far the present invention has been discussed with reference to an open hole, however, the present invention can as well be applied in a cased hole. In that case, calculating the pressure gradient along the hydrocarbon-bearing formation layer starts with making a plurality of perforation sets through the casing wall into the formation layer. Then the tool is lowered in the cased borehole to the first perforation set. The tool is further provided with an upper and a lower packer arranged at either side of the inlet of the central conduit, wherein the distance between the upper and the lower packer is larger than the height of a perforation set, and wherein the spacing between adjacent perforation sets is at least equal to the length of the longest packer. The packers are set so that the perforation set is straddled between the packers. Then formation fluid is allowed to enter into the fluid receptacle, the pressure build-up is measured, and the fluid pressure is determined. Then the tool is positioned near the next perforation set, and the fluid pressure is measured and so on, until the fluid pressures of a predetermined number of locations have been measured. From these fluid pressures and the true vertical depths of the casing sets, the pressure gradient is calculated.

What is claimed is:

1. A method of determining at least one of the in situ PVT properties of a hydrocarbon reservoir fluid that is present in a hydrocarbon-bearing formation layer traversed by a borehole, which method comprises the steps of:

a1) providing a first tool, said first tool comprising a central conduit having an inlet and outlet and being provided with a pressure sensor;

b1) lowering said first tool into said borehole to a first location;

c1) establishing exclusive fluid communication between said formation and the inlet of said central conduit and measuring formation fluid pressure;

d1) repeating step c1) for a plurality of new locations;

e1) calculating along the hydrocarbon-bearing formation layer the pressure gradient for each location from the plurality of formation fluid pressure measurements; and f1) determining at least one in situ PVT property from the pressure gradients utilizing a relationship in which a formation pressure gradient has been empirically related to the at least one PVT properties for similar hydrocarbon bearing formation layers.

2. The method according to claim 1, wherein the borehole is cased and wherein the step of calculating the pressure gradient along the hydrocarbon-bearing formation layer according to step e1) comprises the steps of:

a5) making a plurality of perforation sets through the casing wall into the formation layer;

b5) providing said first tool, said first tool further comprising an upper and a lower packer arranged at either side of the inlet of the central conduit, wherein the distance between the upper and the lower packer is larger than the height of said first perforation set, and wherein the spacing between adjacent perforation sets is at least equal to the length of the longest packer;

c5) lowering said tool from b5) into said cased borehole to the first perforation set;

d5) setting the packers so that the first perforation set is straddled between the packers, allowing formation fluid to enter into the fluid receptacle, measuring the pressure build-up, and determining the fluid pressure;

e5) repeating step d5) for the remaining of said plurality of perforation sets; and f5) calculating the pressure gradients for each perforation set.

3. The method according to claim 1, wherein said relationship is established comprising the following steps:

a2) providing a second tool, said second tool comprises a central conduit having an inlet and being provided with a pressure sensor, a fluid receptacle having an inlet opening into the central conduit, and at least one fluid storage chamber;

b2) lowering said second tool to the first of a set of locations in said formation layer;

c2) making an exclusive fluid communication between the formation and the inlet of the central conduit, allowing formation fluid to enter into the fluid receptacle, and measuring the pressure build-up until no change in measured pressure is observed to obtain the fluid pressure;

d2) transferring a portion of the formation fluid from the fluid receptacle to one of said fluid storage chambers;

e2) repeating steps c2) and d2) for the remaining locations of said set of locations;

f2) retrieving said second tool from the borehole and calculating the formation layer pressure gradients for each location in said set of locations;

g2) testing the fluid samples from said second tool to calculate PVT properties for the formation fluid samples; and h2) correlating the PVT properties to the formation layer pressure gradients.

4. The method according to claim 3, wherein making an exclusive fluid communication between the formation and the inlet of the central conduit comprises extending into the formation a probe having an outlet that is in direct fluid communication with the inlet of the central conduit of the tool.

5. The method according to claim 4, wherein making an exclusive fluid communication further includes activating a heating device arranged near the probe to heat the formation fluid.

* * * * *